(12) United States Patent
Laush

(10) Patent No.: US 6,321,587 B1
(45) Date of Patent: Nov. 27, 2001

(54) SOLID STATE FLUORINE SENSOR SYSTEM AND METHOD

(75) Inventor: Curtis T. Laush, Austin, TX (US)

(73) Assignee: Radian International LLC, Austin, TX (US)

( * ) Notice: Subject to any disclaimer, the term of this patent is extended or adjusted under 35 U.S.C. 154(b) by 0 days.

(21) Appl. No.: 09/687,345

(22) Filed: Oct. 13, 2000

Related U.S. Application Data

(60) Provisional application No. 60/159,831, filed on Oct. 15, 1999.

(51) Int. Cl.$^7$ ............................. G01N 21/05; G01N 21/62
(52) U.S. Cl. ..................... 73/23.2; 73/31.05; 324/464; 356/437
(58) Field of Search ................................. 73/23.2, 28.02, 73/31.05; 324/464; 356/437

(56) References Cited

U.S. PATENT DOCUMENTS

| | | | |
|---|---|---|---|
| 4,377,436 | * 3/1983 | Donnelly et al. | ........................ 438/16 |
| 4,637,938 | * 1/1987 | Lee et al. | ................................... 427/8 |
| 4,847,207 | * 7/1989 | Birks et al. | ............................ 436/120 |
| 6,133,740 | * 11/2000 | Wentworth et al. | .................. 324/464 |

FOREIGN PATENT DOCUMENTS

| | | | |
|---|---|---|---|
| 4419466-A1 | * 11/1994 | (DE) . | |
| 03152445-A | * 6/1991 | (JP) | ................................... 250/458.1 |

\* cited by examiner

*Primary Examiner*—Hezron Williams
*Assistant Examiner*—Michael Cygan
(74) *Attorney, Agent, or Firm*—Klauber & Jackson

(57) ABSTRACT

A gaseous fluorine detection system is provided which includes a generally enclosed sample cell containing a substrate comprising a material which interacts with fluorine gas to generate radiant energy. A gas sample of fluorine, the concentration levels of which are to be evaluated is flowed through the cell. A photomultiplier tube is positioned to receive the resulting radiant energy and generate an electrical output signal related to the level of said radiant energy. Means are provided for measuring the said photomultiplier output signal and relating same to the fluorine concentration of the gas sample provided to the cell.

9 Claims, 4 Drawing Sheets

Fluorine Concentration vs. Detector Signal

SOLID STATE FLUORINE SENSOR SYSTEM AND METHOD

RELATED APPLICATION

This application claims priority from Applicant's provisional patent application, filed Oct. 15, 1999 under Ser. No. 60/159,831.

FIELD OF INVENTION

This invention relates generally to analytic methods and apparatus, and more specifically relates to a system for use in carrying out measurements of gas samples extracted from semiconductor tool exhausts, or derived from other environments of interest. The invention is also applicable to process control applications related to general chemical process environments.

BACKGROUND OF INVENTION

Chemical emissions from the manufacturing processes used in the semiconductor industry represent serious occupational and environmental hazards and as such are closely regulated.

The use and associated emissions of perfluorocompounds (PFCs) as suspected greenhouse gases within the semiconductor industry have indeed received increased attention in recent years. The 1997 Kyoto Protocol provided the impetus for major industries to address global warming issues, and the semiconductor industry has taken a proactive response toward PFC emissions reduction. The World Semiconductor Council (WSC), comprised of the European Electronic Component Manufacturer's Association (EECA), the Electronics Industry Association of Japan (EIAJ), the Korean Semiconductor Industry Association (KSIA) and the Semiconductor Industry Association (SIA) agreed in 1999 to reduce the aggregate absolute emissions of PFCs from semiconductor fabrication facilities to greater than 10% from the baseline year by the year 2010 (the baseline year for EECA, EIAJ, and SIA was set at 1995, and KSIA's at 1997). These goals address greenhouse gas emissions without affecting competitiveness, and allow for a uniform set of guidelines for suppliers and researchers world-wide. Similar PFC reduction initiatives have also been included in the SIA "International Technology Roadmap for Semiconductors" and relationships have been formed between federal regulatory agencies and industry, such as the 1995 memoranda of understanding (MOU) between the EPA and the US semiconductor industry. To attain such goals, it is estimated that PFC emission reductions of 90% for wafer etch and 95% for plasma enhanced chemical vapor deposition (PECVD) chamber cleans compared to 1995 levels will be required for existing 200 mm wafer fabs.

Given the industry's reliance on PFC usage in wafer fabrication, the Roadmap's challenge is compelling. To achieve such a goal requires an aggressive approach involving process optimization, alternative chemistries, PFC recapture/recycle and/or abatement. Beyond the development and implementation of innovative solutions, which are already well underway, accurate characterization techniques are also needed to assess the effectiveness of these solutions. Decisions can then be made based on empirical results, leading to direct reductions in PFC emissions and proper handling of any subsequent chemical by-products.

Because PECVD chamber clean processes can account for 60–90% (with dielectric etch processes accounting for 10–30%) of PFC emissions from 200 mm wafer manufacturing fabs, plasma abatement and nitrogen trifluoride ($NF_3$)-based chamber cleaning approaches have recently been evaluated within the industry. These approaches have proven to be extremely effective in PFC reduction, but introduce an ancillary challenge, namely the characterization and abatement of molecular fluorine ($F_2$). Concerns include the emission of HF or other regulated toxic compounds into the air, as well as discharge of ionic fluoride transferred from wet scrubbers into the site's wastewater stream, which can potentially exceed a site's fluoride emission permit. Increased fluoride emission from approaches to reduce PFC emissions can challenge these fluoride ion wastewater discharge limits. The degree to which fluorine will require special treatment depends on the ability to accurately measure concentrations emitted from manufacturing processes in real-time.

SUMMARY OF THE INVENTION

Now in accordance with the present invention, a sampling and analysis system and method is provided for the detection and quantification of gaseous diatomic fluorine, an extremely pernicious product which is found in semiconductor process tool exhaust streams, as well as in other industrial and related environments. In the latter regard, for example, it is often of intense interest from a viewpoint of pollution abatement, to be able to monitor the fluorine gas concentrations in acid exhaust streams or in the discharge streams from other industrial processes.

In accordance with the present invention, the gas sample to be analyzed is flowed through an enclosed cell that allows interaction with an organic substrate provided at one end thereof. A corrosive gas rotometer provides a measure of gas flow as it is exhausted from the cell. The substrate consists of a sodium salicylate paste applied to the end of a sapphire disk that is exposed to the cell contents. The back end of the substrate is mated with a photomultiplier tube (PMT) that provides a sensitive measure of the amount of radiant energy liberated from the interaction of fluorine with the sodium salt. A picoammeter is used to detect the current output from the PMT and is interfaced to a computer configured with appropriate software. The chemical interaction is reproducible and easily characterized under laboratory conditions, so that a relationship between detector output and fluorine concentration is established before field measurements are taken. After calibration of the substrate response against known fluorine standards, the result is a chemical sensor that provides detection and, after the calibration curves are applied to the measured current signals, quantification of $F_2$ in real-time. Concentrations are displayed and archived continuously. The device components are packaged such that the entire system is portable and field rugged.

DESCRIPTION OF PREFERRED EMBODIMENT

Figure 1:
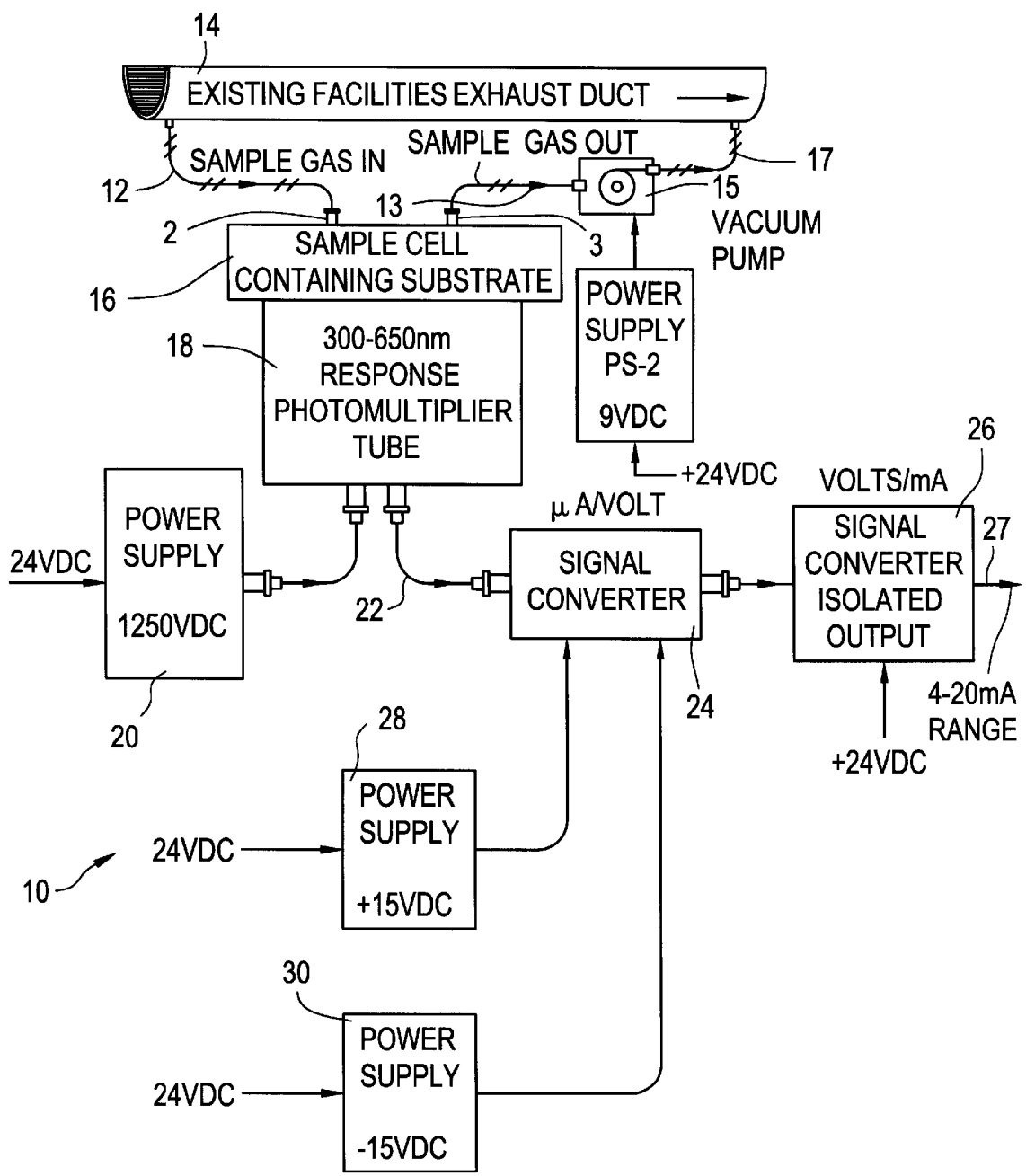
FIG. 1 is a schematic block diagram of a system in accordance with the invention.
Figure 2:
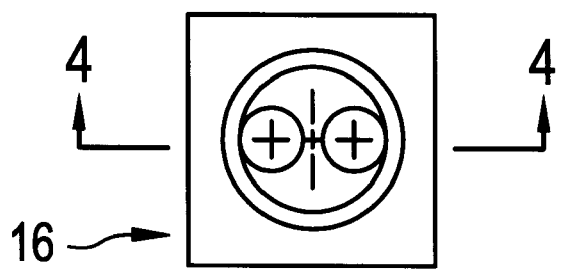
FIGS. 2 and 3 are respectively top and end elevational views of a cell utilizable in the present system; the window is removed for clarity.
Figure 3:
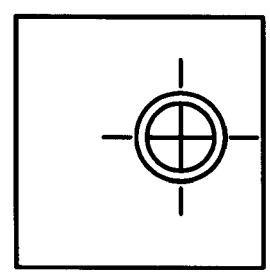
Figure 4:
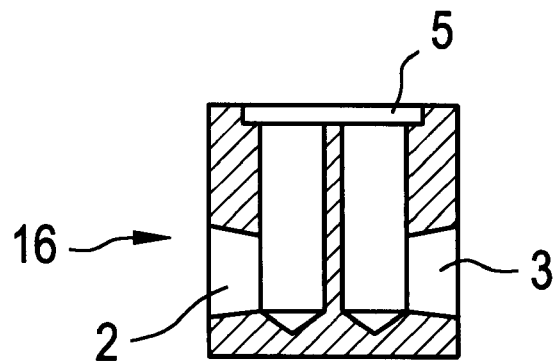
FIG. 4 is a cross-sectional view of the cell of FIGS. 2 and 3, taken along the line 2–2' of FIG. 2.

In FIG. 1, a schematic block diagram appears of a fluorine sensor system 10 that allows for the continuous, real-time detection of $F_2$ in gaseous streams. System 10 can be applied as either an in-situ or extractive exhaust stream monitoring device. The extractive configuration depicted in the FIG. 1 illustrates how a slipstream 12 may be drawn from an exhaust duct 14 through a small sample cell 16 via cell inlet 2 at moderate (<5 slpm) flow. FIGS. 2, 3 and 4 depicting the cell 16, may be considered simultaneously with this description. The sample gas is moved through the cell 16 by a vacuum pump 15 which draws the gas from cell 16 via an outlet 3 and line 13 and returns the gas to duct 14 via line 17. The cell 16 is designed such that the sample gas will uniformly interact with a sodium salicylate substrate deposited on a window, typical dimensions of which can e.g., be 25 mm diameter×2 mm thick. The cell is made of a machined block of aluminum, which is nickel plated to minimize the interaction with fluorine (or derived gases such as hydrogen fluoride) with the cell walls. The window is seated in its own groove 5 (with a corrosion-resistant O-ring) and is made of sapphire. The substrate is applied by finely spraying a saturated solution of sodium salicylate in methanol on the sapphire window surface, then allowing ample time (several hours or more) for the substrate to dry before use. As the methanol evaporates an opaque, white residue adheres to the window as a film. The window's back end is in close proximity (not more than 15 mm in distance) to a head-on photomultiplier tube (PMT) 18 with a spectral response range of 300–650 nm. The PMT is provided with power from power supply 20. The PMT gain is typically of the order of $2\times10^6$. The nanoamp level current output 22 from PMT 18 can be detected by a commercial picoammeter, preferably pre-amplified to the milliamp range 27 required to drive common data acquisition circuits by signal converters 24 and 26, the power supplies for which are seen at 28 and 30. The chemical interaction between $F_2$ and sodium salicylate is believed to effect a chemical interaction which causes the substrate to fluoresce in a reproducible and calibrated fashion, as discussed in the following paragraph, so that a mathematical relationship between detector output and $F_2$ concentration is established.

Figure 5:
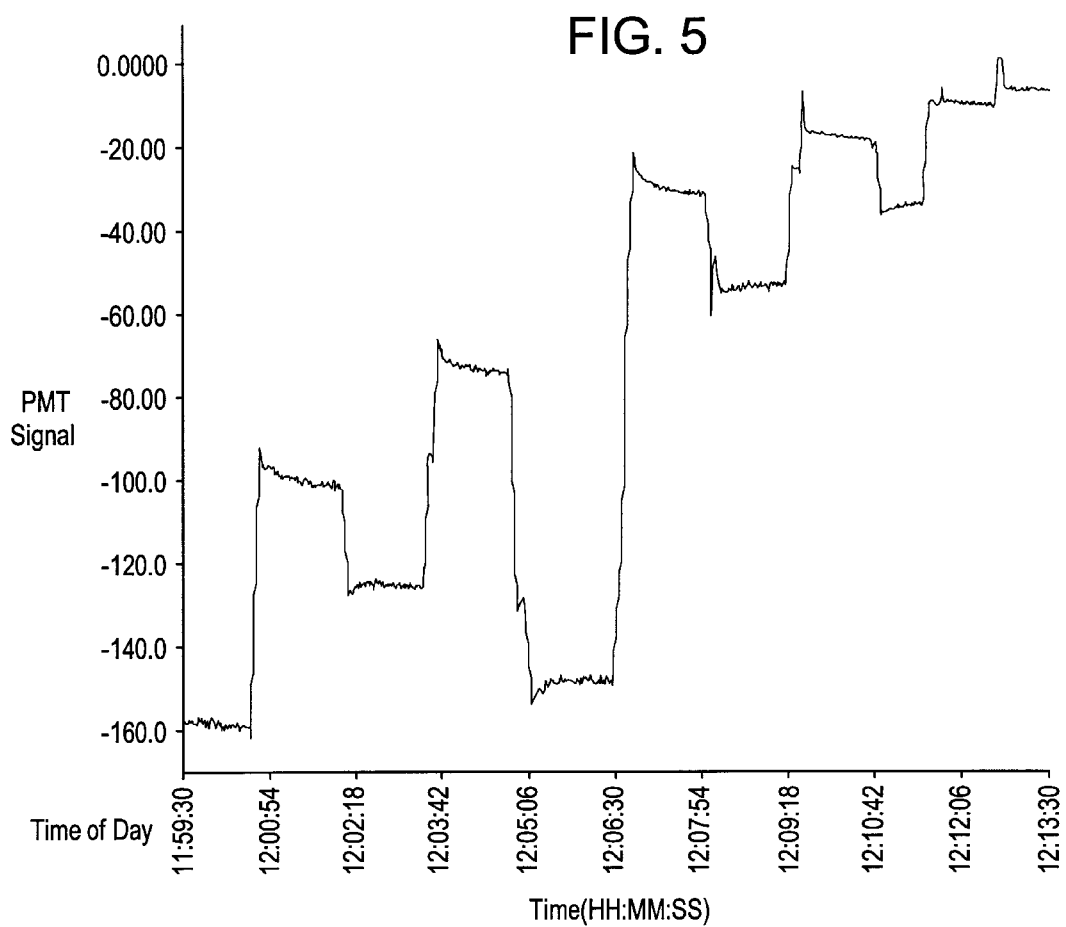
FIG. 5 is a graph depicting an example of raw field calibration data within an expected measurement range for fluorine emissions at a plasma abatement device.
Figure 6:
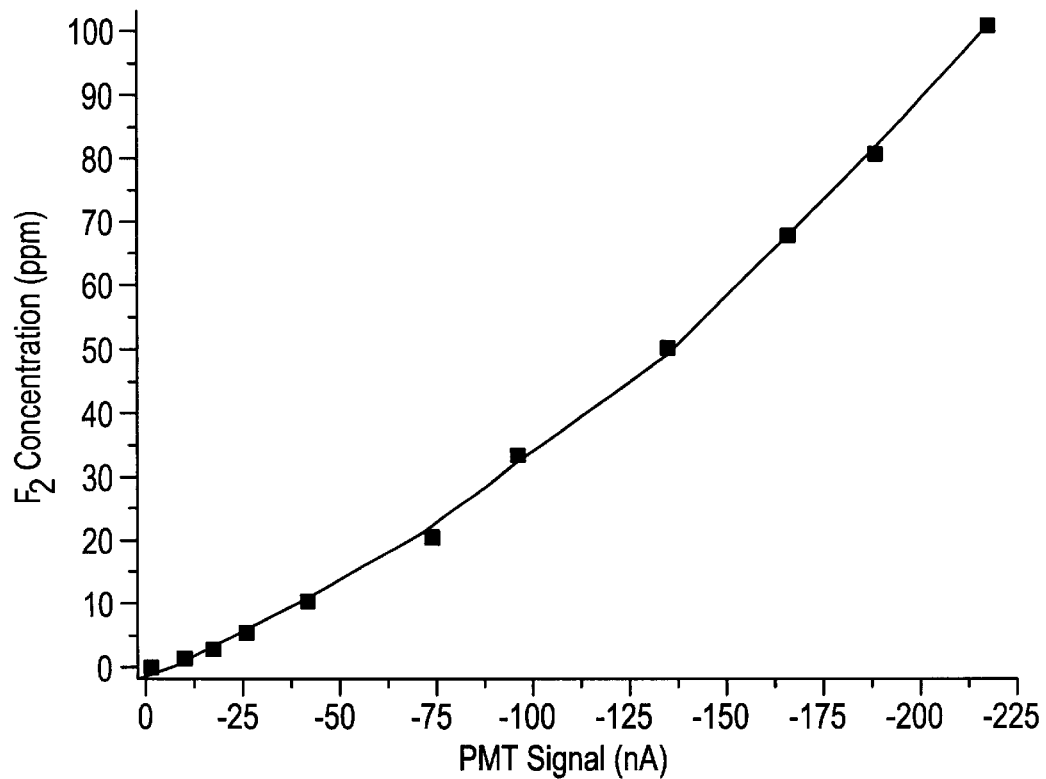
FIG. 6 is a graph characterizing the instrument response based on the data in FIG. 5.

Instrument calibration can be performed in either laboratory or under field conditions using certified $F_2$ gas standards diluted with ultra-high purity nitrogen under precise flows delivered by mass flow controllers and a dilution manifold. FIG. 5 shows an example of raw field-calibration data within an expected measurement range for $F_2$ emissions at a plasma abatement device. The ordinate represents the PMT response in current (expressed as negative nanoamps). The values along the x-axis represent times of day (each collected data point is time stamped). Basically, each level, or data "shelf" corresponds to the PMT output at a given calibration spiking level ($F_2$ introduced into the cell 16 at a known concentration level) while allowing a little time for stabilization. Spiking levels were deliberately staggered to preclude the possibility of "memory effects", a constant over-estimation of sensor response due to residual $F_2$ present during sequential step-downs from higher levels. Field calibrations are typically performed in triplicate to verify reproducibility and accuracy before curve fitting. The second order polynomial expressed in FIG. 6 shows the PMT current levels (x-axis) plotted against the known $F_2$ concentration (y-axis) to produce a calibration function that mathematically defines the detector's response. This characterizes the system response for all low to moderate level real-time concentration measurements (0–1000 ppmv; spiking levels from 100–1000 ppmv were performed, but not shown in FIG. 6). Calibrations at high concentrations (1000 ppmv to percentage levels) exhibit a reproducible, but linear behavior.

Statistical analyses of the field calibration data, along with additional high concentration level runs were performed to define the operating and performance specifications tabulated below in Table 1. As shown, the system 10 provides a sensitive, real-time monitoring device for gaseous $F_2$ with a robust design. The sensor was also subjected to various ambient air mixtures containing fluorinated or chlorinated compounds (such as HCl, $Cl_2$, $SiF_4$, HF, etc.) to gauge cross interference effects. No detectable responses are observed from the presence of these chemicals.

TABLE 1

Fluorine Chemical Sensor Operating and Performance Specifications

| | |
|---|---|
| Measurement range | 0 to percentage levels (>10000 ppmv) |
| Measurement precision | ±2% |
| Minimum detection limit | 10 ppbv |
| Detector response time | Msec |
| Sample cell operating pressures | mTorr to several atm |
| Footprint | cell/detector: 12" × 3" × 3" |
| Weight | cell/detector: 2 lbs |
| Electrical requirements | 24 VDC |
| Applicable sample matrices | Ambient air; tool effluent (low pressure or $N_2$ diluted), water saturated air or nitrogen streams (wet scrubber outlets) |
| Chemical interferences | None observed for mixtures containing $SiF_4$, HF, $O_2$, $Cl_2$, HCl, PFCs and $H_2O$ |

While the invention has been set forth in terms of specific embodiments thereof, it is to be understood in view of the present disclosure, that numerous variations upon the invention are now enabled to those skilled in the art, which variations yet reside within the present teachings. Accordingly, the invention is to be broadly construed, and limited only by the scope and spirit of the claims now appended hereto.

I claim:

1. A gaseous fluorine detection system comprising:
   a generally enclosed sample cell containing a substrate comprising a material which interacts with fluorine gas to generate radiant energy, said cell being provided with an inlet and outlet to permit gas flow through the cell;
   means to flow a gas sample containing levels of fluorine through said cell for examination;
   a photomultiplier tube being positioned to receive radiant energy resulting from interaction of said substrate material with said fluorine and generate an electrical output signal related to the level of said radiant energy; and
   means for measuring the said photomultiplier output signal and relating same to the fluorine concentration of the gas sample flowing through said cell.

2. A system in accordance with claim 1 wherein the material comprising said substrate which interacts with said fluorine gas is sodium salicylate.

3. A system in accordance with claim 2 wherein the sodium salicylate substrate is deposited on a window provided at the said cell, said window being in proximity to said photomultiplier tube.

4. A system in accordance with claim 3, wherein said window comprises sapphire.

5. A system in accordance with claim 3 wherein the spectral response of said photomultiplier tube is in the range of 300 to 650 nm.

6. A system in accordance with claim 3, further including a signal converter means for receiving the output from said photomultiplier tube and preamplifying the levels of same to a milliamp range, to enable driving of milliamp sensitive data acquisition circuits.

7. A system in accordance with claim 4 wherein the output from said photomultiplier tube is detected by a picoammeter.

8. A method for detecting fluorine in a gas sample, comprising effecting an interaction between said gas sample and sodium salicylate in a generally enclosed cell to generate from said interaction detectable radiant energy;

detecting the generated radiant energy with a photomultiplier tube to thereby generate an electrical output signal related to the level of radiant energy; and calibrating the output signal from said photomultiplier tube as a function of fluorine concentration by measuring output signal levels from the tube when said preceding steps are carried out with known levels of fluorine gas.

9. A method in accordance with claim 8, wherein the sodium salicylate is provided as a deposited film on a sapphire surface, said film and sapphire surface defining a window at a wall of the said cell which is in proximity to said photomultiplier tube to enable receipt at said tube of said generated radiant energy.

* * * * *